United States Patent [19]
Sato et al.

[11] Patent Number: 5,218,212
[45] Date of Patent: Jun. 8, 1993

[54] DEVICE FOR OPTICALLY DETECTING A CHEMICAL CHANGE IN FLUID

[75] Inventors: Susumu Sato, 29-3, Aza-toinoshita, Hiroomote, Akita-shi, Akita-ken; Yoshihiro Togashi, Nagoya; Norio Ito, Nagoya; Koichi Ishii, Nagoya; Shinji Yasuda, Nagoya, all of Japan

[73] Assignees: Mitsubishi Denki Kabushiki Kaisha, Tokyo; Susumu Sato, Akita, both of Japan

[21] Appl. No.: 746,990

[22] Filed: Aug. 19, 1991

Related U.S. Application Data

[63] Continuation-in-part of Ser. No. 531,165, May 31, 1990, Pat. No. 5,075,544.

[30] Foreign Application Priority Data

Nov. 24, 1989 [JP] Japan .................................. 1-305074
Aug. 29, 1990 [JP] Japan .................................. 2-227611

[51] Int. Cl.$^5$ .......................... G01J 3/50; G01N 15/06
[52] U.S. Cl. .................................. 250/573; 250/226; 250/227.23; 356/412
[58] Field of Search ............ 250/227.23, 226, 573–577; 356/402, 412, 437, 136, 135; 422/86, 87; 436/167

[56] References Cited

U.S. PATENT DOCUMENTS

| | | | |
|---|---|---|---|
| 3,998,591 | 12/1976 | Eckfeldt | 422/86 |
| 4,136,566 | 1/1979 | Christensen | 73/356 |
| 4,200,110 | 4/1980 | Peterson et al. | 128/634 |
| 4,471,186 | 9/1984 | Yoshioka | 422/86 |
| 4,560,248 | 12/1985 | Cramp et al. | 356/412 |
| 4,572,447 | 6/1988 | Kimmel et al. | 356/416 |
| 4,661,320 | 4/1987 | Ito et al. | 422/86 |
| 4,851,665 | 7/1989 | Pesquento et al. | 250/227 |
| 4,863,694 | 9/1989 | Kimmel et al. | 422/86 |

FOREIGN PATENT DOCUMENTS 0434893 7/1991 European Pat. Off. .
WO8605589 9/1986 PCT Int'l Appl. .
2054844 2/1981 United Kingdom .

OTHER PUBLICATIONS

Oriel Corporation, *Optics & Filters* vol. III, p. 10–2, 1990.

Primary Examiner—David C. Nelms
Assistant Examiner—Michael Messinger
Attorney, Agent, or Firm—Oblon, Spivak, McClelland, Maier & Neustadt

[57] ABSTRACT

A device for optically detecting a chemical change of fluid comprises a prism placed in fluid to be tested and a layer of color indication material formed on a surface of the prism to thereby detect a chemical change of fluid by means of a transmitted light and a reflected light in the prism.

6 Claims, 5 Drawing Sheets

FILM THICKNESS OF COLOR INDICATION MATERIAL ON PRISM (Å). (a) WAVELENGTH OF 680 nm

FILM THICKNESS OF COLOR INDICATION MATERIAL ON PRISM (Å). (b) WAVELENGTH OF 550 nm

FILM THICKNESS OF COLOR INDICATION MATERIAL ON PRISM (Å). (c) WAVELENGTH OF 440 nm

DEVICE FOR OPTICALLY DETECTING A CHEMICAL CHANGE IN FLUID

This application is a continuation-in-part application of the application Ser. No. 07/531,165 now U.S. Pat. No. 5,075,544 having a filing date of May 31, 1990.

BACKGROUND OF THE INVENTION

1. Field of the Invention

The present invention relates to a device for optically detecting an acidic substance or a basic substance, in particular, to detect fluid which exhibits acidity or basicity.

More particularly, the present invention relates to an abnormality detecting device for detecting, for instance, a degree of deterioration or an abnormal state in an electric apparatus in which the above-mentioned optically detecting device is used.

2. Discussion of Background

Heretofore, a so-called gas filled insulation apparatus wherein $SF_6$ gas or the like having excellent insulating, quenching performance is used as an insulating medium, has been used as a transformer, an interrupter, and for a bus bar or the like.

If an abnormal state takes place in such electric apparatus, and when arcing or corona discharges occur or a short circuit takes place in an electric contact portion due to a fault in contact, such abnormality can not be easily detected from outside because electric components are covered by a metallic casing. Accordingly, when abnormality takes place, it is necessary to take the following steps for the restoration of the electric apparatus: the operation of the electric apparatus is stopped; an insulating medium such as $SF_6$ is recovered; electric assemblies are dismantled; a fault component is detected, the fault component is repaired or replaced, and the electric apparatus is again assembled.

However, the dismantlement of the electric apparatus to inspect and find a fault component requires a large amount of work, there is difficulty in recovering the insulating medium, and it requires much time.

Therefore, a gas abnormality detecting device as in Japanese Unexamined Patent Publication No. 24844/1982 is proposed, for instance. However, the proposed device had a problem that it was difficult to obtain accurately information of abnormality.

There has been a strong demand of providing an optically detecting device capable of detecting a chemical change in fluid such as gas or liquid, especially detecting an acidic substance or a basic substance in the fluid with good sensitivity, for the above-mentioned abnormality detecting apparatus.

SUMMARY OF THE INVENTION

It is an object of the present invention to eliminate the above-mentioned problems and to provide a device for detecting a chemical change in fluid with good sensitivity, which is suited for a large scale production and is produced in a stable manner.

In accordance with the present invention, there is provided a device for optically detecting a chemical change of fluid which comprises a prism placed in fluid to be tested and a layer of color indication material formed on a surface of the prism to thereby detect a chemical change of fluid by means of a transmitted light and a reflected light in the prism.

In accordance with the present invention, there is provided a device for optically detecting a chemical change of fluid to optically detect a color reaction in a thin film of color indication material by means of a transmitted light and a reflected light to thereby detect the absence or presence of an acidic substance or a basic substance in the fluid characterized in that a solid material constituting said thin film is on a surface of a prism and the thickness of said thin film is in a range of 100 Å–600 Å.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

Figure 1A:
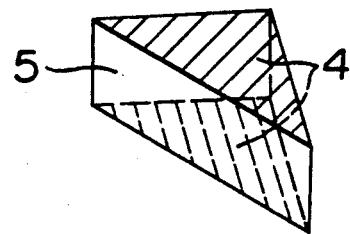
FIGS. 1A and 1B are diagrams showing an embodiment of the device for optically detecting a chemical change in fluid according to the present invention.

The present invention will be described in more detail.

As the color indication material, such a color indication material that a state of electrons in the molecules of the material is influenced by an acidic substance or a basic substance, and the spectra of light by the absorption and reflection is changed to thereby show a color reaction, is usable. Accordingly, by detecting the change of the spectrum of light with good sensitivity, it is possible to detect a color reaction which has not been able to distinguish the reaction through naked eyes.

In accordance with the above-mentioned principle, a color indication material is placed in the neutral atmosphere; the color indication material is irradiated with light from a light source including a wavelength of light which is changed by a color reaction inherent in the color indication material, and analysis of the wavelength of light reflected or absorbed is conducted whereby the presence or absence of the color reaction, namely, the presence or absence of an acidic substance or a basic substance and a degree of an acidic atmosphere or a basic atmosphere can be detected.

The detection of a color reaction with use of a prism as a substance to fix the color indication material is conducted as follows. The prism is generally understood in that incident light is entirely reflected at wall surfaces (side surfaces) of the prism. However, in fact, light slightly leaks from the side faces of the prism to the outside and the leaking light again enters into the prism. Accordingly, by attaching the color indication material to the side faces of the prism, it is possible to detect a color reaction in the color indication material, if any, when light which has entered in the prism and has been reflected in it becomes output light. Then, a change in the light absorption characteristics of the color indication material can be detected. In this case, when the film thickness of the color indication material is large, light passing through the prism does not pass through a portion where the color reaction takes place (because the color reaction occurs at a surface side of the film), whereby the color reaction can not be detected at all. On the other hand, when the film thickness is small, the quantity of the color reaction is small and, therefore, sensitivity becomes low.

Accordingly, there is the optimum value in the film thickness of the color indication material. If a film of color indication material having the optimum thickness and uniform thickness is obtained, the sensitivity in detecting optically the color reaction is excellent.

The film thickness of the color indication material is preferably in a range of 100 Å–600 Å. In particular, it was confirmed experimentally that the optimum value of the film thickness was a range of about 300 Å–400 Å. In order to form a thin film of color indication material on the prism, a vacuum deposition method is preferably used. Thus, in accordance with the present invention, optically detecting devices of the present invention having good sensitivity can be stably produced at a large scale production rate.

In accordance with the present invention, a device for optically detecting a chemical change in fluid (hereinbelow, referred to as an optically detecting device) wherein a color indication material in a form of a thin film which is sufficient to detect a color reaction is formed on the surface of a prism is used, wherein light which has leaked from the surface of the prism is reflected and transmitted in the prism. The light reflected and transmitted in the prism is subjected to a spectral analysis so as to measure the intensity of light for each spectrum. The intensity of light measured is converted into an electric output, which is calculated in the diagnosis device, whereby the presence or absence of a color reaction, namely, the presence or absence of an acidic substance or basic substance is judged.

Preferred embodiments of the optically detecting device of the present invention will be described with reference to the drawings.

Figure 1B:
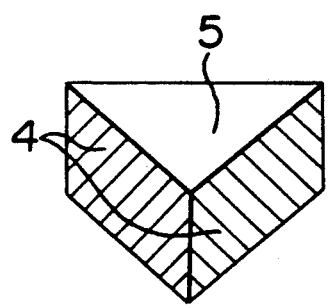

FIG. 1 is a diagram showing how the color indication material 4 is fixed to a surface or surfaces of the prism 5. The combination of the color indication material 4 and the prism 5 constitutes an embodiment of the present invention. Specifically, in case of using a crystal violet, a water solution of crystal violet is applied to the surface or surfaces of the prism and the prism is dried to thereby solidify the water solution.

Figure 2A:
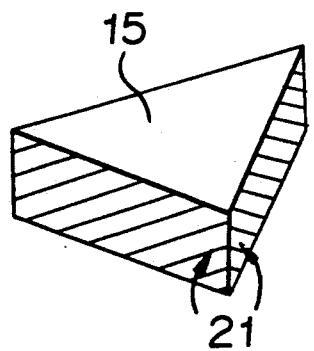
FIGS. 2A and 2B are diagrams showing another embodiment of the optical device similar to that in FIG. 1 according to the present invention.
Figure 2B:
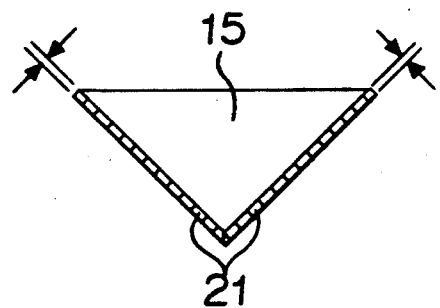

FIG. 2 shows an another embodiment of the optically detecting device of the present invention.

In FIG. 2, reference numeral 15 designates a prism and numeral 21 designates a color indication material having a film thickness in a range of 100 Å–600 Å.

FIG. 3 shows a result of examination as to the transmittance of light passing through the prism, i.e. the ratio of the intensity of an incident light entering in the prism to the intensity of an output light from the prism, at different wavelengths before and after the color reaction wherein crystal violet is used as a color indication material, and the thickness of the thin film of crystal violet on the prism as shown in FIG. 1 is changed.

Figure 3A:
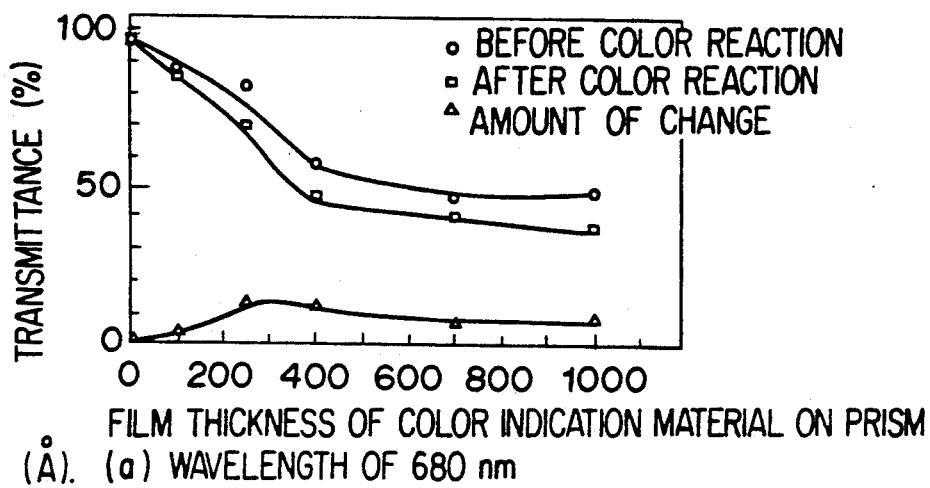
FIG. 3a, 3b and 3c are graphs showing the relation between the film thickness of a color indication material and the transmittance, and an amount of change in transmittance respectively.
Figure 3B:
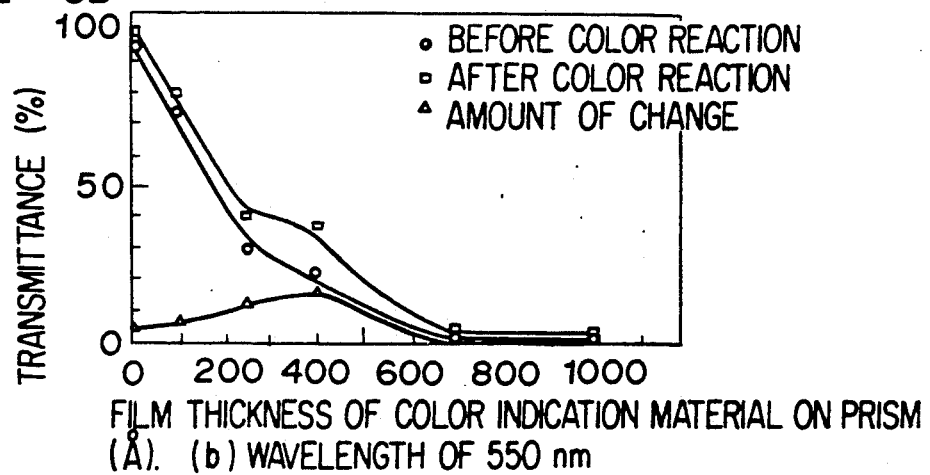
Figure 3C:
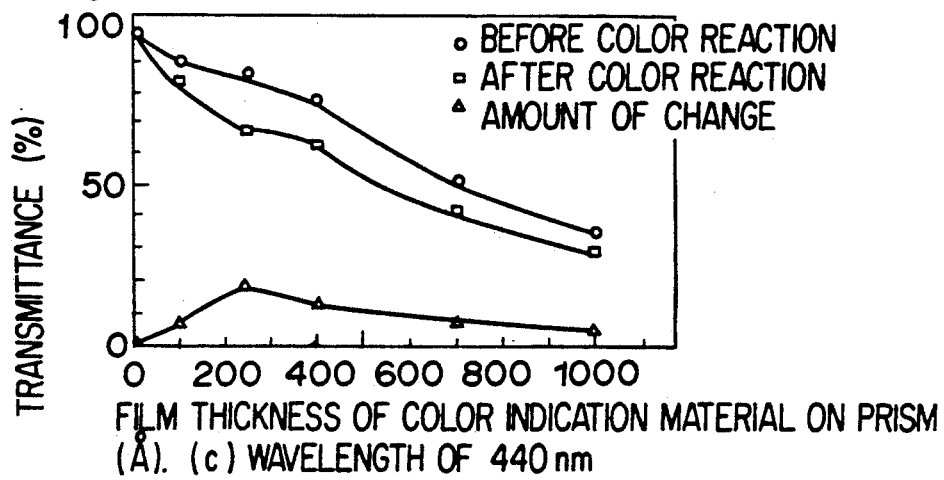

In FIGS. 3a, 3b and 3c, the abscissa denotes the film thickness of the color indication material and the ordinate denotes the transmittance at wavelengths of 680 nm, 550 nm and 440 nm respectively. In the Figures, symbols ◯ represent values before the color reaction, symbols ☐ represent values after the color reaction and symbols Δ represent amounts of change of the transmittance between before and after the color reaction. Further, the Figures show the reaction of the crystal violet to an acidic substance as a change of the transmittance at several spectra wherein the wavelengths represent the portion exhibiting the greatest change in the reaction color of the crystal violet. FIGS. 3a, 3b and 3c clearly show that the change of the transmittance exhibits the greatest value in each of the wavelengths in a range of film thickness of 300 Å–400 Å. Namely, by using the above-mentioned film thickness, a slight amount of an acidic substance can be detected with good sensitivity.

FIGS. 3a–3c, however, clearly show that use of the film thickness in a range of 100 Å–600 Å permits observation of a change of the transmittance for each of the wavelengths, it is possible to detect an acidic substance or a basic substance.

In the above-mentioned embodiments, the thin film of color indication material is formed on the surface of the prism by means of a vacuum deposition method. The nature of the thin film of color indication material formed by vapor depositing is determined depending on the thickness of the thin film, an evaporating material used and a process of vapor deposition. An organic material can be used for the color indication material. Since the organic material has a low decomposition temperature of molecules, a high evaporation temperature can not be expected. The crystal violet in a case that the crystalline contains no water exhibits entirely different colors from a case that it contains water, and the crystalline containing water exhibits a violet color. In consideration of the above-mentioned conditions and in order to prepare a thin film of crystal violet in a stable manner, the inventors of the present application have developed the measures as follows.

A color indication material is dissolved in an organic solvent; the organic solvent is dried to recrystallize the color indication material, and the recrystalline of the material is subjected to a vapor deposition method to thereby form a thin film of color indication material. By using the above-mentioned method, the color indication material having a desired thickness can be formed on the surface of the prism. Thus, by controlling the film thickness of the color indication material, an optically detecting device capable of detecting an acidic substance or a basic substance with good sensitivity can be provided.

In the above-mentioned method, since the color indication material is dissolved in the organic solvent and the solution is dried to recrystallize the material, the crystalline of the color indication material can be small, whereby the evaporation temperature can effectively be suppressed to be low, and the characteristics of the thin film formed by vacuum deposition can be improved.

Figure 4:
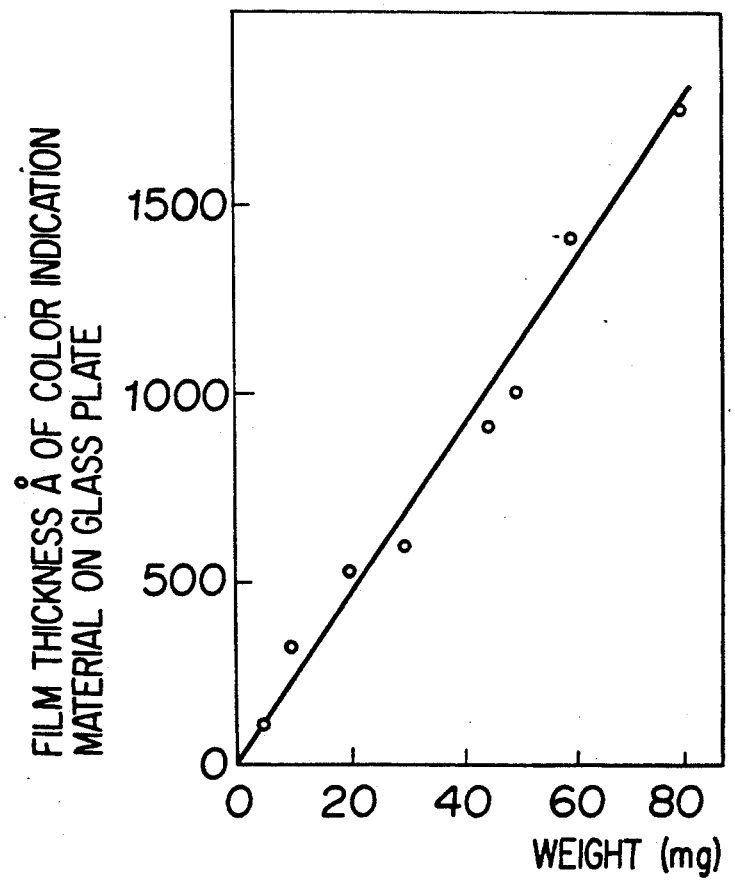
FIG. 4 is a graph showing the relation between an amount of a color indication material in a crucible and the film thickness on the prism.

FIG. 4 is a graph showing the relation of the weight of the color indication material in a crucible to the thickness of a thin film of color indication material which is formed on the surface of a glass plate by vapor deposition under the condition that the degree of vacuum and the evaporation temperature are constant in a vacuum metallizing furnace. The thickness of the thin film of color indication material on the glass plate is measured with an interference microscope. FIG. 3 shows a linear characteristic which passes the origin. Accordingly, it is understood from the above-mentioned graph that the thickness of the thin film can be easily controlled.

In the following, an embodiment of the abnormality detecting device in which the optically detecting device of the present invention is used will be described with reference to the drawings.

Figure 5:
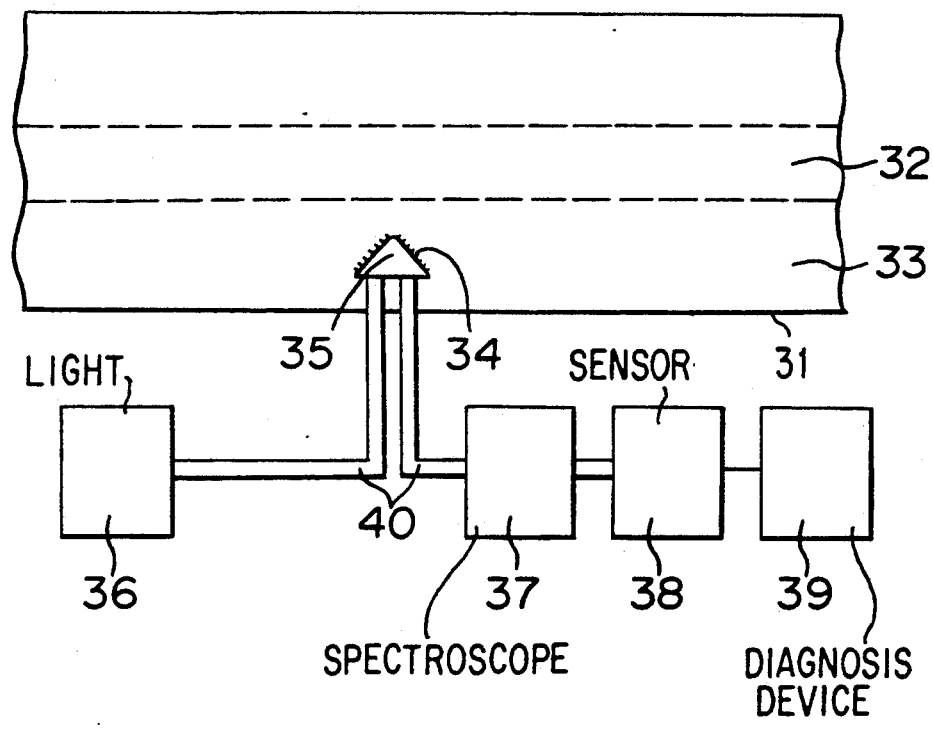
FIG. 5 is an embodiment of an abnormality detecting apparatus for an electric machine in which the optically detecting device of the present invention is used.

In FIG. 5, a reference numeral 31 designates a vessel having a grounded terminal which is used for a gas filled insulating apparatus, a numeral 32 designates a metallic conductor for the gas filled insulating apparatus, a numeral 33 designates SF$_6$ gas, a numeral 34 designates a color indication material, a numeral 35 designates a prism which fixes the color indication material in an insulating medium (the combination of the color indication material 34 and the prism 35 constitutes the optically detecting device of the present invention), a numeral 36 designates a light source such as a tungsten lamp which emits light including a wavelength band region which changes by a color reaction, a numeral 37 designates a spectroscope as a spectral decomposing device for light which reaches through the prism 35, a numeral 38 designates a photomultiplier tube (photomultiplier) as a sensor for the light which has been subjected to spectral decomposition, a numeral 39 designates a diagnosis device which operates the output of the photomultiplier 38 to determine the presence or the absence of deterioration or abnormality, and a numeral 40 designates optical fibers for transmitting light from the light source 36 to the spectroscope 37 through the prism 35.

The function of the abnormality detecting device of the present invention will be explained in accordance with FIG. 5.

Let's assume that the SF$_6$ gas is filled in the vessel 31 having a grounded terminal in a gas filled insulating apparatus and there takes place an arc discharge by any cause on the metallic conductor to which a high voltage is applied. The SF$_6$ gas is decomposed by the arc discharge whereby a product, which is represented by the following formula, is produced by the reaction with a small amount of water contained in the apparatus:

$$(n/2)SF_6 + M \rightarrow (n/2)SF_4 + MF \qquad (1)$$

where M: a metal electrode and n: the chemical bond valence of the metal M.

Further, HF gas as a strong acidic gas is produced by the chemical reaction as follows:

$$SF_4 + H_2O \rightarrow SOF_2 + 2HF \qquad (2)$$

$$SOF_2 + H_2O \rightarrow SO_2 + 2HF \qquad (3)$$

Thus, by disposing a color indication material such as the crystal violet in the grounded vessel 31 so that there causes the color reaction of the color indication material to a strong acidic gas such as HF produced by the decomposition by discharge and the hydrolysis of SF$_6$, the color indication material exhibits a color reaction by the acidic gas. There has been known that the crystal violet exemplified here shows a blue or purple color as a basic color and an yellow color as an acidic color. Thus, by detecting a change in the color indication material by the color reaction, it is possible to detect the decomposition of the SF$_6$ gas by arc discharging, namely, gas produced by the decomposition of the SF$_6$ gas. However, it was impossible to judge the deterioration of insulators or products resulted from the deterioration with high sensitivity through observation by naked eyes. The principal object of the present invention is to obtain a device capable of detecting with high sensitivity the color reaction of a color indication material to thereby detect the presence of gas produced by the decomposition of SF$_6$.

It is said that in a prism, the total reflection of an incident light is caused at wall surfaces of the prism. However, in fact, a small amount of light leaks from the wall surfaces of the prism to the outside and the leaked light returns into the prism. In view of the fact, by attaching a color indication material on the wall surfaces of the prism, the light reflected from the prism show a spectrum corresponding to the color peculiar to the color indication material due to the absorption characteristic of light of the material.

When, for instance, an acidic gas is produced by arc discharging in an electric apparatus, there causes a change of color by the color reaction of a color indication material, and the spectrum of the reflected light is different from the spectrum as seen before the color reaction.

Figure 6:
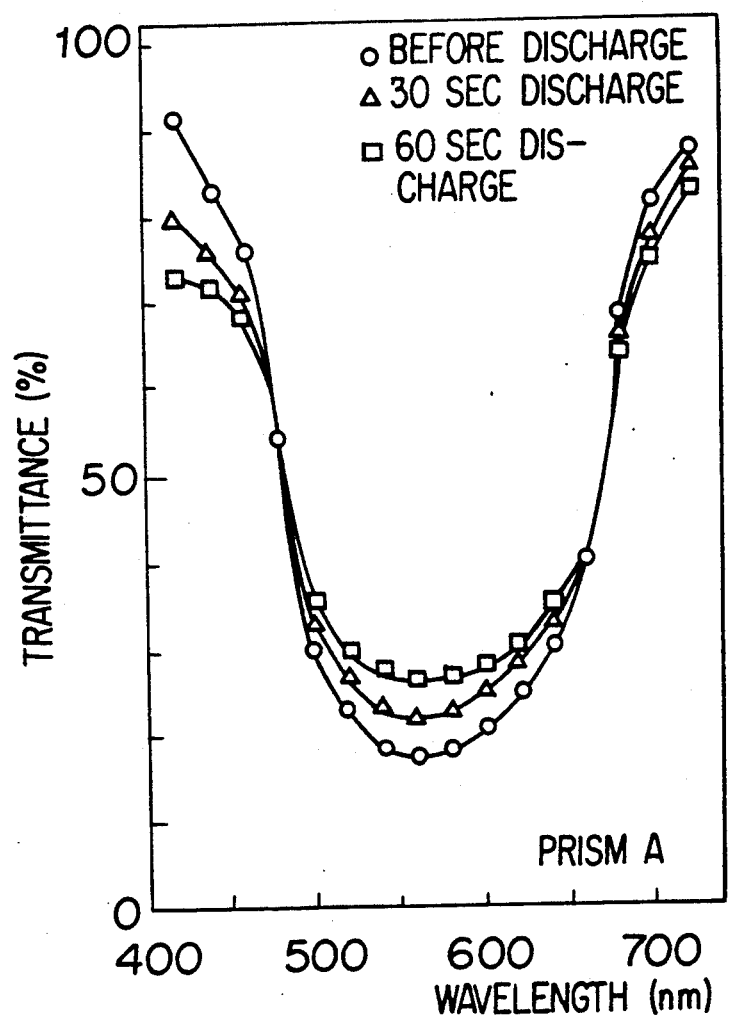
FIG. 6 is a diagram showing a result of experiments conducted according to the principle of the present invention.

FIG. 6 is a diagram showing a result of measurement of the spectral distribution of light reflected from a prism, in terms of a ratio of reflected light to incident light, i.e. transmittance, before and after electric discharge wherein a simulation electrode and a prism on which a crystal violet is coated are placed in a SF$_6$ gas-filled deciccator, and electric discharges are forcibly caused at the simulation electrode. In FIG. 6, the abscissa represents wavelength (nm) and the ordinate represents transmittance (%). FIG. 6 shows each spectral distribution to wavelengths before an electric discharge, and after a 30 sec electric discharge and a 60 sec electric discharge. As is apparent from FIG. 6, the transmittance increases by electric discharges at or around a wavelength of 550 nm, and the transmittance decreases at a wavelength region shorter than about 450 nm and a wavelength region longer than about 700 nm. This implys that the crystal violet shows an yellow color as an acidic color. In accordance with the above-mentioned principle, the crystal violet shows a color reaction in an acidic gas atmosphere by the decomposition of SF$_6$ gas.

The function of the structural elements of the present invention is to detect the change of a spectrum to thereby determine deterioration or abnormality in insulators. The function of each of the elements will be described.

Light emitted from the light source 36 is introduced into the prism 35 through optical fibers 40. Light reflected from the prism 35 on which the color indication material 34 is applied, is introduced into the spectroscope 37 through the optical fibers 40. A spectrum obtained by the spectroscope 37 is detected by the photomultiplier 38 to be converted into an electric signal. The diagnosis device 39 detects a wavelength which changes due to a color reaction, e.g. the intensity of light having a wavelength of about 550 nm when the crystal violet is utilized as the color indication material 34, and generates an alarm in the determination that an insulator becomes deteriorate or abnormal when the intensity of light having the wavelength reaches a predetermined value.

The diagnosis device 39 will be described in more detail. The fact that the color of the crystal violet as a color indication material changes to an yellow color by the reaction with an acidic gas implys that the reflectivity of light having a wavelength of about 550 nm increases. Detection by naked eyes is allowed only when the difference in reflectivity becomes significant. In order to detect the difference of reflectivity with high sensitivity, the following measures may be utilized, for instance. A white light is irradiated to a color indication material through a prism, and light reflected from the prism is subjected to spectral decomposition. In the spectrum of the reflected light, an attention is made to the greatly changed wavelength. When it is assumed that the output of the light source 36, i.e. the intensity of the white light is constant, the intensity of light reflected by the prism 35 on which the color indication material 34 is applied changes its wavelength depending on conditions of the color indication material 34. The diagnosis device 39 generates an alarm when the intensity of light at a wavelength around 550 nm reaches a predetermined level. The diagnosis device 39 can be constructed easily by applying electronics. In some cases, it is possible for human to judge an electronic apparatus by observing the output in terms of wavelength of the photomultiplier 38.

In the above-mentioned embodiment, description has been made as to a technique of judging the deterioration or the abnormality by detecting the intensity of light at or around a wavelength of 550 nm. However, the following measures may be taken. For instance, by utilizing such tendency that the transmittance of light is improved at or around a wavelength of 550 nm by the color reaction and the transmittance is reduced at a wavelength region more than 700 nm, a ratio of the intensity of light at or around 550 nm to the intensity of light of more than 700 nm is used, and when the ratio reaches a predetermined level, an alarm may be generated, whereby it is possible to obtain a diagnosis for an electric apparatus with higher sensitivity than that as in the embodiment described before.

In FIG. 6, the transmittance of light at or around 550 nm before the initiation of electric discharge and after 60 sec electric discharge are respectively 18% and 26%. There is the difference of about 1.4 times therebetween. On the other hand, the transmittance of light at or around 700 nm under the above-mentioned conditions are respectively 82% and 76%. Accordingly, values in percentage of the transmittance at 700 nm/the transmittance at 550 nm before the initiation of electric discharge and after 60 sec electric discharge are respectively $82\%/18\% \approx 4.6$ and $76\%/26\% \approx 2.9$. Therefore there are the difference of about 1.6 times therebetween.

With respect to the abnormality detecting device as shown in FIG. 5, it is possible to diagnose an electric apparatus as to whether or not deterioration or abnormality occurs by arranging the abnormality detecting device of the present invention in a vessel filled with gas in the apparatus. In this case, it is unnecessary to dismantle the electric apparatus, and therefore, inspection can be made quickly, when any abnormality is found. A time for restoration is small.

In the above-mentioned embodiment, the crystal violet is used as a color indication material. However, another color indication material such as Bromocresol Purple may be used. Further, in the above-mentioned embodiment, the white light, which is obtainable by a tungsten lamp, a halogen lam or the like, is used. However, an LD, an LED or the like may be used so long as a light source has a spectral distribution of light having a wavelength band region which changes by a color reaction.

In the above-mentioned embodiment, the spectroscope is used as a spectral decomposing device, and the photomultiplier tube is used as a photosensor. However, they may be unified.

In the above-mentioned embodiment, the prism is used as a fixing member for fixing a color indication material in an insulating medium whereby light entering into the prism through optical fibers is totally reflected and the reflected light is further transmitted through optical fibers. As such fixing means, a glass plate or a mirror may be used.

In FIG. 5, only the color indication material 34, the prism 35 and the optical fibers 40 may be arranged in the electric apparatus wherein a connector or connectors are provided at the optical fibers 40 so that the other structural elements are connected by using the connector or connectors when they are needed. Further, the device as shown in FIG. 5 is equipped in each electric apparatus so that a signal of each of the devices is observed.

In accordance with the present invention, an optically detecting device capable of detecting optically a color reaction in a thin film of color indication material in an optical manner by using a transmission light and a reflection light in the prism to thereby detect an acidic substance or a basic substance, wherein a solid material constituting the thin film is formed on the surface of the prism is used. Particularly, the film thickness of the thin film is determined in a range of 100 Å–600 Å. Accordingly, the acidic substance or a basic substance can be detected with good sensitivity.

Although the crystal violet is used as the color indication material in the above-mentioned description, bromocresol purple can also be used. Further, another color indication material may be used depending on the object of detection and usage.

In accordance with the present invention, since the thin film is formed by using a vacuum deposition method, a desired film thickness can be correctly obtained, whereby an optically detecting device capable of detecting an acidic substance or a basic substance with good sensitivity can be produced in a stable manner and large scale production.

Further, the present invention is applicable to the detection of water pollution or air pollution other than the abnormality diagnosis of an electric apparatus or appliance described above.

Obviously, numerous modifications and variations of the present invention are possible in light of the above teachings. It is therefore to be understood that within the scope of the appended claims, the invention may be practiced otherwise than as specifically described herein.

What is claimed is:

1. A device for optically detecting a chemical change in a fluid comprising:
   a light source;
   a prism placed in said fluid and receiving light from said light source;
   a layer of color indication material having a thickness in a range of 100 Å–600 Å formed on a surface of said prism, said received light being reflected by said layer of color indication material, said reflected light having a change in color due to a change in said color indication material caused by a chemical change in the fluid;

means for detecting the color change and thereby detecting the chemical change in said fluid.

2. The device according to claim 1, wherein the layer of color indication material is formed by coating a water solution of the color indication material on the surface of the prism and drying.

3. A device according to claim 1, wherein the thickness of said layer is in a range of 300 Å–400 Å.

4. A device for optically detecting a chemical change in a fluid comprising:

a light source;

a prism for receiving light from said light source;

a thin film of color indication material formed on a surface of said prism, the thickness of said thin film being in the range of 100 Å–600 Å, said thin film having a color reaction due to the absence or presence of an acidic substance or basic substance in the fluid, said color reaction causing a change in color in the reflected light.

5. A device according to claim 4, wherein said thin film is formed by vapor deposition.

6. A device according to claim 4, wherein the thickness of said thin film is in the range of 300 Å–400 Å.

* * * * *